Figure 1:
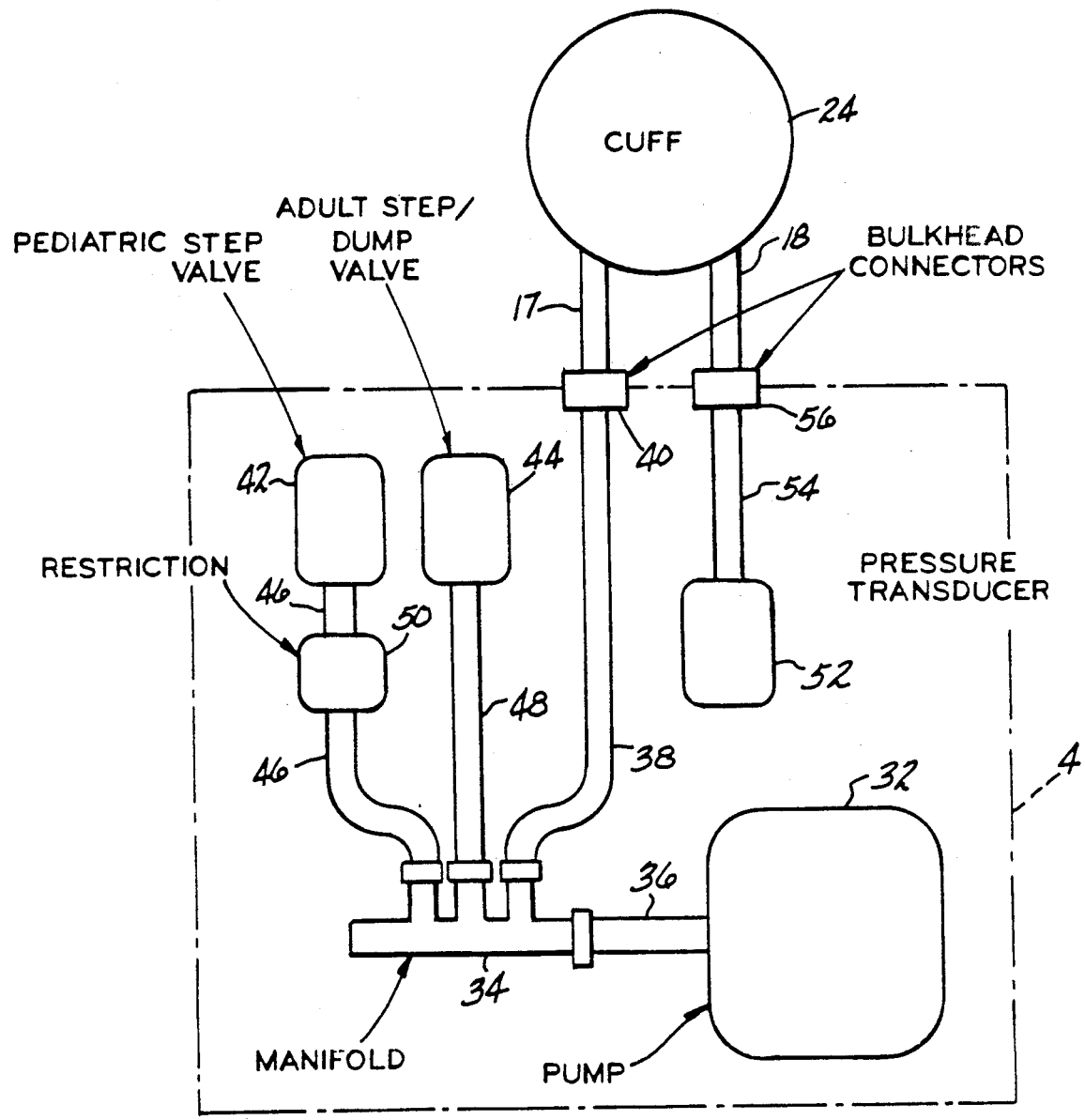

United States Patent [19]

LaViola

[11] Patent Number: 5,022,403

[45] Date of Patent: Jun. 11, 1991

[54] AUTOMATIC BLOOD PRESSURE MEASURING DEVICE AND METHOD WITH CUFF SIZE DETERMINATION

[75] Inventor: John LaViola, Orange, Conn.

[73] Assignee: CAS Medical Systems, Inc., Branford, Conn.

[21] Appl. No.: 24,662

[22] Filed: Mar. 11, 1987

[51] Int. Cl.$^5$ ............................................... A61B 5/02
[52] U.S. Cl. ...................................... 128/680; 128/685
[58] Field of Search ............... 128/672, 677, 680, 681, 128/682, 685

[56] References Cited

U.S. PATENT DOCUMENTS

| | | | |
|---|---|---|---|
| 4,417,586 | 11/1983 | Jewett | 128/685 |
| 4,501,280 | 2/1985 | Hood, Jr. | 128/686 |
| 4,587,974 | 5/1986 | Link | 128/685 |
| 4,605,010 | 8/1986 | McEwen | 128/686 |
| 4,669,485 | 6/1987 | Russell | 128/679 |

FOREIGN PATENT DOCUMENTS 1163327  3/1984  Canada ............................... 128/677

*Primary Examiner*—Stephen C. Pellegrino
*Assistant Examiner*—David Shay
*Attorney, Agent, or Firm*—William W. Jones

[57] ABSTRACT

The device measures blood pressure automatically using the oscillometric technique wherein cuff pressure is deflated stepwise in dynamically determined increments while cuff pressure oscillations are sensed at each cuff pressure level and stored in a computer incorporated into the device. Stepwise cuff deflation is continued until the cuff pressure is below the subject's diastolic pressure whereupon the cuff is automatically deflated. The device can be used with different sized cuffs specific for different patient categories. For example, the device can employ an adult cuff, or a pediatric cuff. To accomodate the different cuff sizes, the device has more than one bleed orifice with which it controls the deflation steps. The onboard computer is programmed to use a selected one of the bleed orifices in the first bleed step and to use the time duration of the first bleed step to determine what size cuff is being used. Once the cuff size is determined, the proper bleed orifice designed for the determined cuff size is made operative, and the testing continues. This minimizes the effects of cuff pressure on the arm, and the selection gives the most efficient deflation characteristics.

1 Claim, 2 Drawing Sheets

AUTOMATIC BLOOD PRESSURE MEASURING DEVICE AND METHOD WITH CUFF SIZE DETERMINATION

This application discloses an improvement of an invention disclosed in copending application Ser. No. 892,848, filed Aug. 1, 1986 and assigned to the assignee of this application, and the subject matter of which is specifically incorporated herein in its entirety. More particularly, this invention relates to an improved blood pressure measuring device which includes a provision for determining what size pressure cuff is being used with the device, and then proceeding with the appropriate measuring format.

The measurement of systolic, diastolic and mean blood pressure values by measuring cuff pressure oscillations caused by blood vessel pulses during stepwise deflation of the cuff is a known technique. Methodology and apparatus for automatically performing this general technique are disclosed in U.S. Pat. No. 4,349,034 granted Sept. 14, 1982 to M. Ramsey and U.S. Pat. No. 4,360,029 granted Nov. 23, 1982 to M. Ramsey. These patent disclosures relate to a technique which uses a computer controlled device to inflate a pressure cuff, stepwise deflate the cuff, measure and store cuff pressure oscillations occuring at each deflation plateau, and determine which cuff pressure oscillation was the largest. The device then identifies the cuff pressure at which the largest oscillation took place as the mean blood pressure. Provisions are made for rejecting artifact cuff pressure oscillations which can result from subject movement, accidental contact with the pressure cuff, and the like.

A device similiar to that disclosed in the aforesaid patents is described in an article authored by Joseph Erlanger, M.D., published in *The Johns Hopkins Hospital Reports* Vo. XII by the Johns Hopkins Press (1904). In the Erlanger device, the cuff was automatically inflated to an initial pressure above mean, and then stepwise deflated to a pressure below mean. Cuff pressure oscillations were sensed and traced onto a rotating drum sheet by a floating pen. Artificial oscillations are apparent upon viewing the trace. Further, U.S. Pat. No. 4,501,280 granted to R. Hood, Jr. discloses methodology for identifying the size of a blood pressure system cuff. This patent discloses a technique whereby the cuff is inflated to a predetermined level and then the air release valve is pulsed. Measurement of the time necessary for the pulse to propagate to the cuff and back to the monitor is used to determine the size of the cuff attached to the monitor. Subsequent inflation, deflation, and operation of the monitor follows an appropriate format based upon that cuff size determination.

This invention is directed to an improved oscillometric procedure which utilizes a stepwise deflation of the cuff format while obtaining more accurate systolic, diastolic and mean blood pressure readings. The device includes a pressure cuff for affixation to the subject and a pump which automatically inflates the cuff to an initial pressure, which is calculated to be above the subject's systolic pressure. Operation of the pump, as well as the other components of the device, is controlled by an onboard computer. The device includes two different sized bleed orifices, one suited for use with younger, smaller persons, such as pediatric patients, and the other of which is suited for adult patients. The technician will select the proper cuff for whatever patient is being tested. After being connected to the selected cuff, the device will be started and will inflate the cuff to a preselected pressure. The first bleed step will be performed through the smaller of the orifices. The device will time the interval required to deflate the cuff to the first selected lower step and will compare the measured interval to a calculated target interval. If the measured interval is shorter than the target interval, then the device knows that the cuff being used is the smaller of the two cuff choices. If the measured interval is longer, then the larger cuff is being used. If the device senses the smaller cuff the deflation steps are continued with the smaller orifice. If the larger cuff is sensed then the device closes the smaller orifice and opens the larger, whereupon the deflation steps are continued.

It is therefore an object of the invention to provide a device for automatically measuring blood pressure by the non-invasive oscillometric method.

It is an additional object of this invention to provide a device of the character described which may be used with a variety of cuff sizes adapted for particular classes of patients.

It is another object of this invention to provide a device of the character described which automatically detects the size cuff being used and, if necessary, adjusts further operations to conform to the sensed cuff size.

Figure 2:
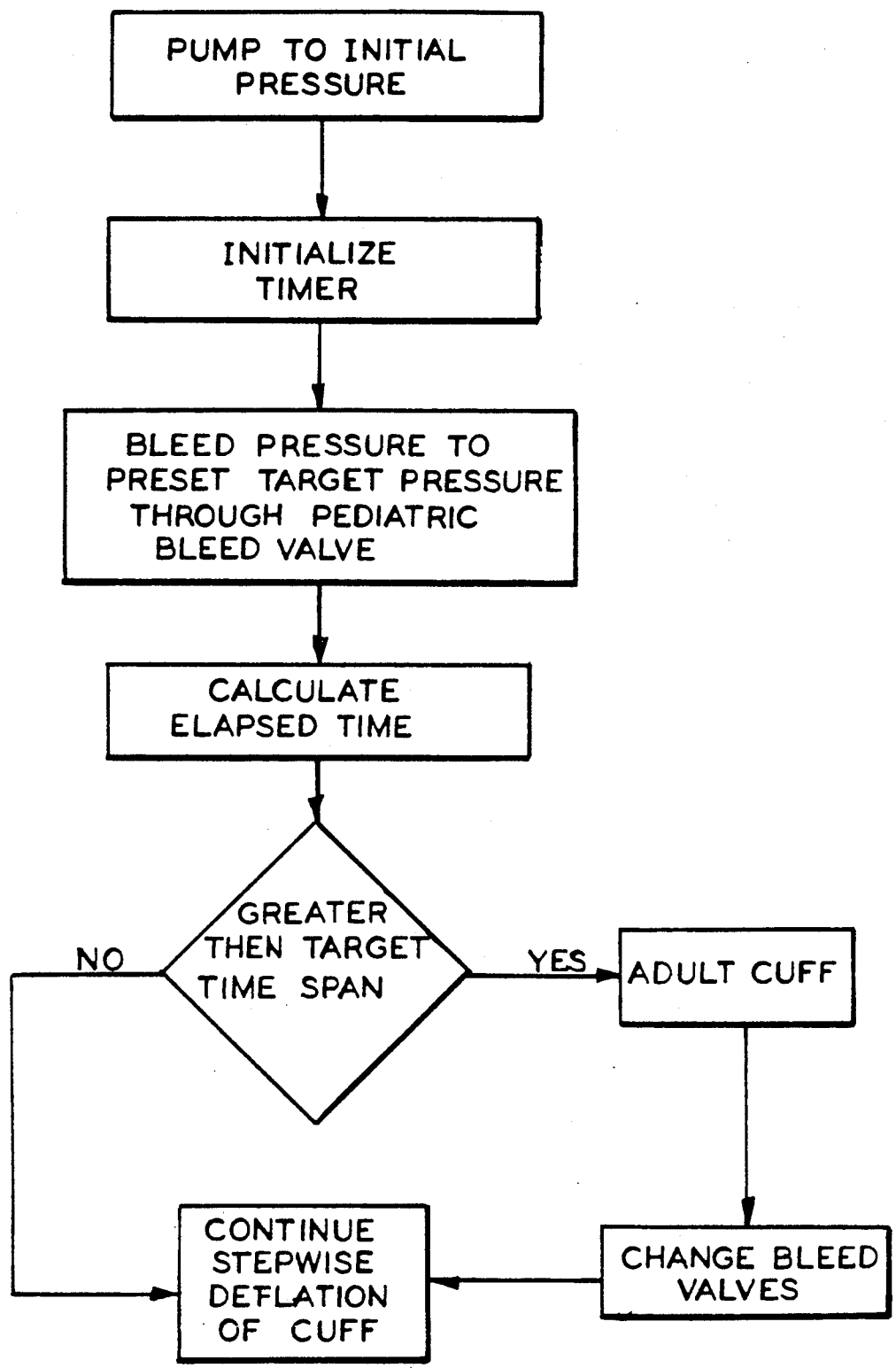

These and other objects and advantages of this invention will become more readily apparent from the following detailed description of a preferred embodiment when taken in conjunction with the accompanying drawings, in which:

FIG. 1 is a schematic representation of the physical components of the device; and FIG. 2 is a flow chart of the software used to perform the cuff size determination.

Referring now to FIG. 1, there is shown, somewhat schematically, the mechanical pneumatic components of the device as they are arranged in the housing 4 (shown in phantom). The cuff 24 is connected to an inflation hose 17 and a cuff pressure/oscillation detector hose 18. An electrically operated pneumatic pump 32 is mounted in the housing 4 and is connected to a manifold 34 via a hose 36. The manifold 34 is connected via a hose 38 to a fitting 40 communicating with the inflation hose 17. A pair of venting valves 42 and 44 are connected to the manifold 34 by hoses 46 and 48 respectively. The valve 42 is a first step valve which provides the controlled stepwise deflation of the cuff 24, and the valve 44 is a second step valve which is used to provide an alternative controlled stepwise deflation of the cuff 24 and which is also used to empty the cuff 24 quickly in one bleed. Interposed between the manifold 34 and the step valve 42 is a restriction 50 comprising a small orifice which serves to slow the flow of air from the manifold 34 to the step valve 42. This element will be used in deflating the cuff to measure the blood pressure of children. The valve 44 does not operate in conjunction with the restriction 50 and thus the valve 44 is used to control deflation of the cuff for adult patients. A pressure transducer 52 is connected to the pressure oscillation detector hose via a hose 54 and fitting 56. The transducer 52 monitors the pressure in the cuff 24 as well as oscillations in the cuff pressure caused by arterial pulses.

The device, with the aid of the software described hereinafter, is able to automatically determine whether the patient is a child or an adult during the first deflation step after the initial inflation, and, once the type of patient is determined, the device will automatically adjust its mode of operation accordingly. In taking the blood pressure of a subject, the operator will secure a pediatric size cuff to a pediatric subject, and an adult size cuff to an adult subject. The device will then determine which size cuff is being used in the following manner. When the device is turned on it will inflate the cuff to a predetermined initial pressure of about 175 mm Hg and will always use the pediatric step valve 42 which operates in concert with the restriction 50 to make the first incremental drop in pressure. The microprocessor will know when the step valve 42 is opened and the transducer will detect when the pressure in the cuff has reached a predetermined first lower pressure step. The reaching of this first lower pressure step will be relayed to the microprocessor which will then close the valve 42. The time span between opening of the step valve 42 and reaching the first lower pressure step will be measured and compared to a target time span. If the actual elapsed time is greater than the target time span then the microprocessor will know that the cuff is an adult cuff and will use the valve 44 for all succeeding pressure step drops. Likewise, if the actual elapsed time is less than the target time span, then the microprocessor will know that the cuff is a pediatric cuff and will continue to use the valve 42 for the succeeding stepwise drops in pressure.

The target time span can be, for example, 0.5 sec., or any interval depending on the bleed orifice sizes used. FIG. 2 discloses the software flow chart which controls the aforesaid cuff size determination.

It will be readily appreciated that the device of this invention can be used with either adult or pediatric patients, and can quickly determine whether it is connected to an adult cuff or a pediatric cuff. Once the cuff size is determined this device makes an appropriate operational adjustment, if necessary, and then continues with the blood pressure measurement cycle. The invention also ensures that the patient will not be adversely affected by the pressure of the cuff on the arm.

Since many changes and variations of the disclosed embodiment may be made without departing from the inventive concept, it is not intended to limit the invention otherwise than as required by the appended claims.

What is claimed is:

1. An automatic blood pressure measuring device of the non-invasive oscillometric type, said device comprising:
   (a) a cuff (for girdling an appendage of a subject whose blood pressure is to be measured);
   (b) pump means operably connected to said cuff for inflating the latter;
   (c) first and second valve means operably connected to said cuff for bleeding air therefrom in stepwise fashion, said first valve means being (adapted for use with a pediatric size cuff), and said second valve means being (adapted for use with an adult size cuff);
   (d) microprocessor means operably connected to said pump means and connected to said first and second valve means for controlling operation of the device, said microprocessor means being operable to initiate inflation of said cuff to a predetermine initial pressure, and said microprocessor means further being operable to activate said first valve means to deflate said cuff from said initial pressure to a first calculated lower pressure;
   (e) pressure sensor means operably connected to said microprocessor means to signal said microprocessor means when said first calculated lower pressure is reached in said cuff;
   (f) said microprocessor means including means to determine the lapsed time between actuation of said first valve means and reception of a signal from said pressure sensor means indicative that cuff pressure has reached said first calculated lower pressure, and said microprocessor also including means for comparing said lapsed time with a target time span; and
   (g) means for closing said first valve means and opening said second valve means when said lapsed time is greater than said target time span, whereby continuation of the blood pressure measurement cycle will be via said second valve means.

* * * * *

UNITED STATES PATENT AND TRADEMARK OFFICE
CERTIFICATE OF CORRECTION

PATENT NO. : 5,022,403

DATED : Jun. 11, 1991

INVENTOR(S) : John LaViola

It is certified that error appears in the above-identified patent and that said Letters Patent is hereby corrected as shown below:

Column 4:

Claim 1, line 7, please delete "(";
           line 8, please delete ")";
           line 13, please delete "(";
           line 14, please delete ")";
           line 15, please delete "(";
           line 16, please delete ")".

Signed and Sealed this

Twentieth Day of October, 1992

Attest:

DOUGLAS B. COMER

*Attesting Officer*       *Acting Commissioner of Patents and Trademarks*